United States Patent
Andrews et al.

(10) Patent No.: US 11,278,451 B2
(45) Date of Patent: Mar. 22, 2022

(54) SYSTEMS AND METHODS FOR A LASER ASSISTED EYE TREATMENT

(71) Applicant: Carl Zeiss Meditec AG, Jena (DE)

(72) Inventors: Delbert Peter Andrews, Oberkochen (DE); Michael Stefan Rill, Jena (DE); Stefan Gräber, Deisenhofen (DE); Julia Werth, Munich (DE); Rupert Menapace, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 438 days.

(21) Appl. No.: 15/759,409

(22) PCT Filed: Sep. 15, 2016

(86) PCT No.: PCT/EP2016/071815
§ 371 (c)(1),
(2) Date: Mar. 12, 2018

(87) PCT Pub. No.: WO2017/046241
PCT Pub. Date: Mar. 23, 2017

(65) Prior Publication Data
US 2018/0177630 A1    Jun. 28, 2018

(30) Foreign Application Priority Data

Sep. 17, 2015 (DE) ............. 10 2015 217 847.1
Sep. 17, 2015 (DE) ............. 10 2015 217 849.8

(51) Int. Cl.
*A61B 5/00* (2006.01)
*A61F 9/008* (2006.01)
(Continued)

(52) U.S. Cl.
CPC .............. *A61F 9/008* (2013.01); *A61B 34/10* (2016.02); *A61B 34/25* (2016.02);
(Continued)

(58) Field of Classification Search
CPC ........... A61B 34/10; A61B 2017/00216; A61F 9/007; A61F 9/008
See application file for complete search history.

(56) References Cited

U.S. PATENT DOCUMENTS

2009/0137993 A1\* 5/2009 Kurtz ................. A61F 9/00736
606/6
2012/0163544 A1 6/2012 Mizrahi
(Continued)

FOREIGN PATENT DOCUMENTS

CN 102811684 A 12/2012
CN 103648449 A 3/2014
(Continued)

OTHER PUBLICATIONS

PCT International Search Report and Written Opinion for International Application No. PCT/EP2016/071815, dated Jan. 11, 2017, 11 pages.
DE Search Report for 10 2015 217 849.8, dated Jun. 2, 2016, 14 pages.
DE Search Report for 10 2015 217 847.1, dated May 30, 2016, 14 pages.

*Primary Examiner* — Michael J D'Abreu
(74) *Attorney, Agent, or Firm* — Patterson Thuente Pedersen, P.A.

(57) ABSTRACT

A computer program product for controlling a laser-assisted eye treatment, configured to encode a system controller with a routine for planning the eye treatment, invention further relates to a laser-assisted eye treatment system including a laser treatment unit and a system controller, to a method for generating control data for a laser-assisted eye treatment system, to a planning method for a laser-assisted eye treatment and to an eye treatment method using a laser beam for treating a patient's eye. The invention provides systems and methods for a fast laser-assisted eye treatment of a patient's eye which improve the security and minimize the risk of a non-optimal eye treatment and enable safe eye treatment planning and a shortening of the critical phase of the eye (Continued)

treatment. Encoding a system controller by a routine for planning the eye treatment is strictly based on an anatomy of a patient's eye.

14 Claims, 10 Drawing Sheets

(51) Int. Cl.
*A61B 34/00* (2016.01)
*A61B 34/10* (2016.01)
(52) U.S. Cl.
CPC .............. *A61B 2034/107* (2016.02); *A61F 2009/00851* (2013.01); *A61F 2009/00878* (2013.01); *A61F 2009/00887* (2013.01)

(56) References Cited

U.S. PATENT DOCUMENTS

2013/0150836 A1\* 6/2013 Bor ................. A61F 9/00831
  606/4
2014/0114296 A1\* 4/2014 Woodley ............. A61B 5/7425
  606/6

FOREIGN PATENT DOCUMENTS

| EP | 2 236 109 B1 | 10/2014 |
| EP | 2 846 258 A1 | 3/2015 |
| WO | WO 2015/025039 A1 | 2/2015 |

\* cited by examiner

404

405

51

51

SYSTEMS AND METHODS FOR A LASER ASSISTED EYE TREATMENT

RELATED APPLICATIONS

This application is a National Phase entry of PCT Application No. PCT/EP2016/071815 filed Sep. 15, 2016 which application claims the benefit of priority to German Application No. 10 2015 217 849.8, filed Sep. 17, 2015, and which application claims the benefit of priority to German Application No. 10 2015 217 847.1, filed Sep. 17, 2015 the entire disclosures of which are incorporated herein by reference.

FIELD OF THE INVENTION

The present invention relates to a computer program product for controlling a laser-assisted eye treatment, configured to encode a system controller of a laser-assisted eye treatment system by a routine for planning the eye treatment. The invention further relates to a laser-assisted eye treatment system comprising a laser treatment unit and a system controller, to a method for generating control data for a laser-assisted eye treatment system, to a planning method for a laser-assisted eye treatment and to an eye treatment method using a laser beam for treating a patient's eye. Last but not least the invention relates to a laser-assisted eye treatment system further comprising a characterization unit and a graphical user interface, configured to communicate information required for an eye treatment workflow.

BACKGROUND

Laser systems are widely used for assistance in characterization and therapy in today's eye surgery. A laser beam which is used for therapy may "cut" tissue of a patient's eye or another material in a patient's eye by photo disruption, remove tissue by ablation or modify tissue by heat effects. Examples for the common use of laser systems in eye surgery are the correction of astigmatism and cataract surgery, where pulsed laser beams, mostly femtosecond laser beams, are applied.

Using these laser-assisted eye treatment systems and methods it is very important to work according to a very high level of security as damage in the eye tissue due to user errors is usually not reversible. Thus eye surgery which is involving laser sequences for therapy reasons has to be very well planned.

At the same time, a workflow for an eye surgery system involving laser therapy sequences is very complex. In particular, there are strong interactions between the imaging of the eye in two dimensions, e.g. by video, and in three dimensions, e.g. by optical coherence tomography (OCT), the determination of the anatomical structures, and the planning of the laser incisions.

Depending on the needed therapy, different aspects of the anatomical structure of the patient's eye, but also the totality of different treatment patterns influence each other. A modification introduced in a first part of a treatment pattern may influence other parts of a treatment pattern.

In manual eye surgery it is known that a surgeon achieves better results after having carried out thousands of surgical interventions, thus having developed vast experience in the complex system of an eye. Laser-assisted eye treatment systems therefore give great assistance in controlling the intervention in this complex system. A planning of the treatment can be done in advance and run on a laser-assisted eye treatment system after having checked the possible effects of the planned treatment.

Many laser systems incorporate a patient interface between the final optics of the laser-assisted eye treatment system and the patient's eye—a configuration often referred to as docking. The patient interface provides an optical medium for the laser beam and it immobilizes the patient's eye, usually using some kind of suction mechanism so that there is no movement of the eye between imaging and laser treatment. However, if attached for too long, the suction can potentially damage the scleral vessels of the eye or cause intraocular pressure spikes. For this reason, it is important to perform the docking phase of the procedure as fast as possible.

EP 2 236 109 B1 discloses a system for defining incisions in an eye by application of laser pulses by generating a geometric reference to a three-dimensional eye model, using a "cut surface editor" to directly define and/or edit an intended incision by a user, e.g. the surgeon, and finally determining the position of the incision relative to the generated geometric reference. It is therefore a system giving maximum freedom for planning such a laser treatment and rapidly introducing modifications. On the other hand, finding the best position of an incision is strongly dependent on the experience of the user. By freely defining or editing the intended incision, the user risks not taking into account all needs and all aspects of the complex system for an optimal eye treatment. Further, this direct definition of the "cut surfaces" requires time during a critical phase of the eye treatment, which is the phase immediately before and during the laser-assisted eye treatment, where the eye usually is docked to the laser-assisted eye treatment system.

Further it is important to organize the communication with a laser-assisted eye treatment system during the definition of the incisions as well as for the eye treatment itself in a safe and autonomous way. US 2014/0114296 A1 discloses a graphical user interface and a workflow for a laser-assisted eye surgery system. The disclosed laser-assisted eye surgery system comprises a single graphical user interface, including a large (touch screen) control panel. The laser-assisted eye surgery system also comprises other user interfaces such as a laser footswitch, a docking control keypad, a patient interface RFID reader, an emergency laser stop button, a key switch and a patient chair joystick control. But all these other user interfaces do not allow the display of data and images as well as a complex workflow so as to give access to this information for active communication with the laser eye surgery system, including choosing data out of a variety of data, choosing a special workflow out of a proposal of alternatives, enter, evaluate and modify data. That is why only a graphical user interface, which is a multifunctional communication device capable of setting system operation parameters, processing user input, displaying gathered information such as images, diagrams and data of characterized structures and displaying representations of planned or proposed interventions, may be used for guidance through the whole workflow of a laser-assisted eye surgery treatment, especially for a highly automatized laser-assisted eye surgery treatment.

Such an eye surgery treatment is a complex process, and there are sequences of the workflow which require a large quantity of information to be displayed simultaneously, thus making the handling sometimes confusing. During the critical laser treatment sequences it is important to display screens which are easy to understand in order to prevent handling errors.

SUMMARY OF THE INVENTION

A problem to be solved by the present invention is therefore to provide systems and methods for a fast laser-assisted treatment of a patient's eye which improve the security and minimize the risk of a non-optimal eye treatment. A safe eye treatment planning and a safe operation of the laser-assisted eye treatment system, including a safe and easy communication with the laser-assisted eye treatment system as well as a shortening of the critical phase of the eye treatment is a particular objective therein.

Embodiments of the invention include a computer program product for controlling a laser-assisted eye treatment which is configured to encode a system controller, which is for example a system controller of a laser-assisted eye treatment system, with a routine for planning the eye treatment. The system controller thus might be an internal controller exclusively configured and used to control the laser-assisted eye treatment system or more concretely to control different components of the laser-assisted eye treatment system. Alternatively, the system controller might be an external controller device or an entity comprising an internal and an external controller device, the external controller device being configured to directly or indirectly communicate with the laser-assisted eye treatment system. The external controller device might be e.g. a personal computer or a server.

The system controller may be realized as a single part controller or comprise several parts, e.g. for controlling different components of the laser-assisted eye treatment system or for controlling different steps of the routine.

The routine for planning the eye treatment can be highly automatized, only presenting a resulting eye treatment plan to be confirmed by the surgeon, e.g. a treatment pattern, a sequence of treatment patterns, especially the position of incisions etc. Alternatively, the routine may comprise manual steps, giving the possibility to the surgeon to choose among alternative clinical objectives and ideal anatomical structures, to confirm characterization data and resulting real anatomical structures or the correction of deformation effects.

For example the routine also includes the executing of the eye treatment by a laser beam, for example being a pulsed laser beam, after being confirmed by a surgeon or another user.

According to the invention, the planning of the laser-assisted eye treatment for an individual patient's eye as laid out in the inventive computer program product for encoding the system controller, as well as the routine for the planning of the eye treatment once encoded in the system controller of a laser-assisted eye treatment system, is strictly based on an anatomy of a patient's eye. All clinical objectives and treatment patterns, e.g. incision patterns, are defined in relation to anatomical structures.

Planning of the laser treatment is thus not done directly by designing, editing or moving the treatment patterns in absolute space, e.g. within the target tissue on an image of the eye on the graphical user interface. Planning is rather done always in relation to the anatomic structures of the patient's eye. E.g., it is the anatomic structure that is confirmed to be okay or declared to be redefined by the surgeon, when a treatment pattern is proposed to him.

The real anatomical structure may not be ignored for obtaining an optimal result of an eye treatment, e.g. for cataract surgery, therefore it is safe to define an eye treatment pattern with reference to this concrete anatomy.

Further and most important, a planning of the eye treatment exclusively based on the anatomy considerably shortens the critical phase of the laser-assisted eye treatment: Using a virtual model eye and/or data acquired on the basis of an external pre-treatment characterization of the patient's eye, the planning phase may be done before entering the critical phase of the eye treatment. Even a laser treatment of an eye comprising different laser treatment "tasks", e.g., sub-patterns for the laser treatment carried out at different locations in a patient's eye can and for example will be planned at once—before starting the active eye treatment. After starting the eye treatment, these sub-patterns will only be reviewed, and—if necessary—adapted via the real anatomy during treatment. The sub-pattern may comprise very different tasks and locations, like an incision in the cornea, a capsulotomy and a weakening of the lens structure or a fragmentation of the lens using a laser treatment. According to the invention, all these different tasks and locations can be planned at once in an uncritical phase. The sub-patterns further may be related and especially aligned to each other, e.g., the lens structure weakening or the lens segmentation may be aligned to an access incision.

In an example embodiment, the computer program product is further configured to encode the system controller by a routine for a planning of the eye treatment strictly in relation to a clinical objective and to an ideal anatomical structure of the patient's eye, e.g. using a virtual model eye. The computer program product is further configured to encode the system controller for a remapping and a review of the eye treatment strictly in relation to a detected real anatomical structure of the patient's eye.

In most cases of a laser-assisted eye treatment, the patient's eye is docked to the laser-assisted eye treatment system to fix its position towards a focused laser beam. It has to be guaranteed that the eye does not move during the laser treatment or between characterization of the eye and laser treatment. Docking the eye to an eye treatment system is generally done by applying a vacuum or another attracting force between the eye and a docking device, e.g. a patient interface. It leads to a deformation of the patient's eye which is maintained during the laser treatment. It is therefore common to perform characterization of the patient's eye while the laser-assisted eye treatment system is docked to the eye. After docking to the patient's eye, characterization is performed, e.g. using a combination of top-view imaging such as video imaging and sectional imaging such as OCT, ultrasound or Scheimpflug imaging. On the basis of these images, definition of the patient's individual anatomy is done either automatically through image analysis or manually by matching graphic overlays to the anatomical surfaces visible in the imagery. These anatomical structures will differ from the model anatomical structures used in planning the laser treatment due to individual variances of the human eye and to deformations caused by the docking apparatus.

The inventive computer program product according to example embodiments of the invention is configured to allow remapping the planned laser treatment patterns from the model anatomy and/or an external pretreatment characterization to the now defined real anatomy of the patient's eye. It is further configured to allow reviewing the planned treatment and modifying if necessary in relation to the real anatomical structures. Finally, the computer program product is configured to encode the system controller to perform desired laser treatment in the tissue space of the patient's eye.

Using embodiments of the invention, no planning steps are required during the critical docking phase of the procedure. Corrections to the original planning can be done in review—by reviewing the anatomy of the eye—if the eye treatment patterns are defined in a way that they cannot be mapped onto the patient's anatomy or if the combination of patterns influence each other in an undesired manner.

In a further example embodiment of this invention, planning may be done on the basis of an external pre-treatment characterization of the patient's eye which still allows for the planning to be performed before docking to the patient's eye. This embodiment has the advantage that the representation of the anatomical structures are nearer to that of the eye after docking and is thus potentially more exact.

It is advantageous, if the computer program product is further configured to encode the system controller by a routine for correcting the planning of the eye treatment by secondary effects. These secondary effects in particular may comprise effects related to a docking of the patient's eye to the laser-assisted eye treatment system and/or effects related to an interaction between different treatment patterns and/or related to movements and/or effects related to an individual variance of the patient's eye.

If the treatment pattern of a laser treatment of the eye consists of different parts, e.g. if different incisions have to be executed, these different parts of the treatment pattern have an influence on each other. Especially if the different parts of the treatment pattern are related to different problems of the eye, an influence of these different parts of the treatment pattern has to be checked and corrected if necessary.

A special example embodiment of the computer program product is divided into different sections representing different functions of the program. It comprises:

A section for storing data on at least an ideal anatomical structure. For example a multitude of ideal anatomical structures is stored, and it is possible to choose one out of these according to the type of the patient's eye and the intended treatment.

A section for storing at least a clinical objective. For example a multitude of clinical objectives is stored, and it is possible to choose one out of these according to the type of the patient's eye and the intended treatment. These clinical objectives might be dimensional values, e.g. a diameter of opening, a grid size, a depth, a security distance, etc. Clinical objectives are only indirectly dependent of the anatomical structures: A diameter of opening might be chosen dependent on a diameter of an eye. A security distance may even be a constant, but always refers to an anatomical structure. Nevertheless, these clinical objective also may be defined in a planning phase before entering the critical phase of the eye treatment.

A section for storing standard treatment patterns and adapting them according to a chosen type of a patient's eye.

A section for treating and storing incoming characterization data for establishing real anatomical structures of a patient's eye.

A section for generating an individual treatment pattern, starting with a standard treatment pattern, related to a virtual eye model and adapting it according to the real anatomical structures of the patient's eye.

For example a section for correcting the individual treatment pattern by secondary effects, e.g. effects related to a docking of the patient's eye to the laser-assisted eye treatment system and/or effects related to an interaction between different treatment patterns and /or effects related to movements and/or effects related to an individual variance of the patient's eye. The correcting can be obtained starting with the given individual treatment pattern. Alternatively the correction can already be taken into account during the generation of the individual treatment pattern.

For example the computer program product is available in one of the following states:

It may be stored in a memory section of the system controller;

It may be stored on a memory device and configured to be communicated by an internal and/or external communication path to the system controller. To give some examples, such a memory device might be an internal or external hard disk drive, a memory stick, a compact disk or comparable devices.

An internal or external communication path might be cable connections, a wireless connection, intranet or internet. A laser-assisted eye treatment system may comprise a communication port to allow a transmission from an external memory device to an internal system controller of the laser-assisted eye treatment system.

Further intermediate memory may be used for transmission between an external memory device and a memory section of the system controller.

The problem is further solved by a laser-assisted eye treatment system for carrying out an eye treatment workflow. An eye treatment using a laser beam is a common method in ophthalmology: The laser beam might be used to "cut" the eye tissue or an artificial eye material, like an intraocular lens (IOL) by photodisruption. It also might be used to "bond" eye tissue together or to simply modify the eye tissue by coagulation. Further it might be used to modify the shape of a part of the eye by laser ablation.

In an example embodiment the laser-assisted eye treatment system is used for cataract surgery as well as for refractive corrections. In general, an eye treatment using a laser beam requires a complex workflow to be carry out on a patient's eye.

The laser-assisted eye treatment system comprises a laser treatment unit with a laser source. For example, the laser source is generating a pulsed laser beam. Further for example the pulsed laser beam is generated by a femtosecond laser source. Especially an infrared femtosecond laser source is applied. It is also possible to use a picosecond laser source. The laser beam may then be guided to a laser applicator which is for example part of the laser treatment unit.

The laser treatment unit further comprises a focusing optics and a three dimensional focus shifting system. By use of the focusing optics, the laser beam may be focused to a position in the eye to be treated. The focus of the laser beam may be displaced by a three-dimensional focus shifting system. Such a three-dimensional focus shifting system for example comprises scanners that allow to displace the focus of the pulsed laser beam within a three dimensional treatment volume.

Last but not least the laser-assisted eye treatment system comprises a system controller, configured to control the laser-assisted eye treatment system, e.g., according to an encoded eye treatment workflow. The controller may be realized as a single part controller or comprise several parts.

The system controller is operatively coupled to the laser treatment unit as well as to other units that might be comprised by the laser-assisted eye treatment system via a communication path.

If the controller comprises several parts, these parts may be physically located at very different positions, i.e. directly attached to the feature of the eye treatment system which is controlled by this part of the controller. The communication path also provides for the communication between the several parts and a control panel.

According to the invention, the system controller is encoded by the computer program product for controlling a laser-assisted eye treatment described above. The computer program product is configured to encode a system controller of a laser-assisted eye treatment system by a routine for planning the eye treatment such that it is strictly based on an anatomy of a patient's eye.

There is no "direct planning" of the eye treatment. It is not possible to directly design, edit or displace a treatment pattern, as it is found to be safe to define an eye treatment pattern with reference to this concrete anatomy, for example corrected by secondary effects like interactions during the eye treatment: The treatment pattern being entirely related to the anatomy of a patient's eye avoids resulting additional errors that may occur, if the surgeon or another user has the possibility to freely edit a treatment pattern, especially an incision pattern. Further it allows to shorten the time of the critical phase of the eye treatment, as the planning may be done before entering the critical phase.

For example, the system controller is encoded by the computer program product such that a planning of the eye treatment is strictly done in relation to a clinical objective and to an ideal anatomical structure of the patient's eye. A remapping and review of the eye treatment is further done strictly in relation to a detected real anatomical structure of the patient's eye. This detected real anatomical structure is obtained by internal characterization data obtained once an eye treatment workflow using the laser-assisted eye treatment system is started.

Even if the internal characterization data is obtained during the critical phase of the treatment, this critical phase of the eye treatment is shortened compared to prior art: In prior art, the surgeon creates the treatment pattern during the critical phase by defining an intended incision within an image of the real structures of the patient's eye. In example embodiments of the current invention, an eye treatment pattern is already planned before the critical phase and just reviewed during the critical phase.

Further, the system controller may be encoded such that the planning of the eye treatment is corrected by secondary effects, e.g. related to a docking of the patient's eye to the laser-assisted eye treatment system and/or to an interaction between different treatment pattern and /or to movements of the eye and/or to an individual variance of the patient's eye.

In an example embodiment, the laser-assisted eye treatment system further comprises a characterization unit. Otherwise, a standby characterization unit may be used instead of a characterization unit comprised in the laser-assisted eye treatment system.

The characterization unit may comprise a three-dimensional imaging and/or measurement system, especially an optical coherence tomography (OCT) system, an ultrasonic system, a Scheimpflug camera or an X-ray system. This system may be combined with a video or other optical imaging system which produces a 2D top view of the eye, like an operation microscope.

In an example embodiment of such a laser-assisted eye treatment system, the characterization unit comprises an observation unit, allowing a continuous observation of the eye treatment process. Advantageously, such an observation unit comprises an operation microscope system.

The operation microscope system may include a microscope head video camera for a continuous monitoring and transmission of the images and an adapter to fix the operation microscope system to the laser treatment unit, e.g. on laser applicator of the laser treatment unit.

The characterization unit is used to image structures of the patient's eye and may be applied before starting the eye treatment by the laser beam. It also may be used during the eye treatment to control its progress or after the eye treatment to verify the results. The characterization unit is for example used to measure data of a patient's eye, but also to allow an overview of the structures and the placement of the eye treatment.

By help of a characterization unit comprised in the laser-assisted eye treatment system, an automatic pattern generation for the treatment, for example in an automatic pattern generation of incisions based on the definition of the real anatomy of the patient's eye that were detected just before the automatic pattern generation results in a very reliable treatment pattern for a directly following execution of the laser treatment.

In a further example embodiment of the laser-assisted eye treatment system, an eye treatment workflow is encoded in the system controller comprising several working steps:
  planning the treatment, which is done strictly in relation to clinical objectives and to ideal anatomic structures of a virtual model eye;
  defining the anatomy of the patient's eye, for example by using the data obtained by a characterization unit comprised in the laser-assisted eye treatment system;
  remapping and reviewing the treatment planning in relation to the real anatomical structure of the patient's eye.
  executing the laser treatment according to the reviewed treatment planning.

For example, the laser-assisted eye treatment system is further comprising a docking unit, which is arranged for establishing a defined relationship between the laser-assisted eye treatment system and a patient's eye to be treated. Such a docking unit may imply the use of a liquid-filled patient interface or of a simple contact glass.

In this case the eye treatment workflow encoded in the system controller for example comprising a working step of docking of the patient's eye to the laser-assisted eye treatment system before carrying out the working step of defining the anatomy.

The workflow encoded to the system controller of the laser-assisted eye treatment system, comprising distinct and well defined working steps, it helps to clearly structure the eye treatment.

If, as being the most common case, the laser treatment of the patient's eye is done to carry out laser incisions, the spatial position planning of the laser incisions is done in the "plan treatment" phase strictly in relation to clinical objectives and to ideal anatomical structures.

In the critical phase, in general after docking of the patient's eye to the laser-assisted eye treatment system, imaging of the patient's eye is performed. The surgeon then only has to check and correct the detection of the anatomical structures. The absolute spatial position of the incisions is then automatically calculated relative to these anatomical structures.

In the review phase, the surgeon can view and confirm the absolute position of the incisions. If corrections are needed, the surgeon can correct the detection of the anatomical surfaces or correct parameters which define the incisions in relation to the anatomical structures. It is not possible to directly manipulate the absolute position of the laser incisions.

In an example embodiment of the laser-assisted eye treatment system the system controller comprises predefined settings. These predefined settings may be categorized.

The predefined settings may be given in form of look-up tables, the surgeon or an assistant may scroll through and choose the best fitting setting.

It is of further advantage, if the predefined settings are categorized. A possible categorization would be e.g. the following: fixed information, surgeon dependent information, patient group dependent information, patient specific information. To give an example for patient group dependent information, there might be different levels of cataracts density to be chosen.

The selection of a setting out of the predefined settings may be possible in a completely automatic way or by requiring additional data to be entered manually.

In a further embodiment, the laser-assisted eye treatment system comprises a first control panel arranged to display a first graphical user interface (GUI) provided by the system controller and configured to communicate information required for the eye treatment workflow.

The graphical user interface allows the user to interact with the laser-assisted eye treatment system in very different ways, e.g., by entering data, displaying data, images and graphics, but also through graphical icons and visual indicators. The actions in a GUI may be performed through direct manipulation of the graphical elements and thus give the possibility of displaying graphics as well as text based information and data on the control panel display.

To "communicate" is used here as a generic term for different actions: It means to access data or information, especially parameters required for the treatment, and/or to choose data or information among a variety of different proposals. It may also include not only to use measured data or information but also to enter or to modify, i.e. to manipulate, data or information of the eye treatment system and/or of a patient's eye.

In a laser-assisted eye treatment system, much information required for an eye treatment workflow has "to be given" to the system either from outside or from internal units of the system to enable a smooth workflow. Even if required information is already proposed by the system, the correctness of the data needs to be approved in most cases. For this purpose, a graphical user interface is applied as a general "communication device" with the system. The graphical user interface is a multifunctional communication device, which is, for example, capable of setting system operating parameters, processing user input, displaying gathered information such as images, diagrams and data of characterized structures, and displaying and modifying representations of planned or proposed interventions.

The information the graphical user interface, or more general the system controller via the graphical user interface, is configured to communicate, is defined dependent on a choice of an eye treatment process.

For example, the laser-assisted eye treatment system further comprises a second control panel arranged to display a second graphical user interface provided by the system controller and configured to communicate a subset of information out of an entire set of information required for the eye treatment workflow. This use of a second control panel arranged to display a second graphical user interface is of special advantage and most helpful for a laser-assisted eye treatment, which is planned strictly based on the anatomy of the eye. But it is also advantageous for other laser-assisted eye treatment systems and methods. It thus may also be used independently of an eye treatment planning strictly based on the anatomy of the eye.

As schematically shown in FIG. 6, there is a great amount and variety of information necessary for an eye treatment workflow that is considered not to be critical, as it might be prepared and communicated in advance before the eye treatment or after the eye treatment. It is not time critical and a correction of a given wrong information is generally possible. On the other hand, a small amount of information to be communicated, especially the information to be dealt with during the eye treatment itself, is considered very critical. An error within these information would be grievous.

While the first graphical user interface gives access to a large amount of data and information, in general to the entire set of information required for the possible eye treatment workflows that might be run on the laser-assisted eye treatment system, the second graphical user interface gives access to a subset of the information and data concerning the eye treatment workflow only: It is the restricted selection of information out of the entire set of information which shall be directly available to the surgeon and which will be used during the laser treatment by him. All additional information is not communicated to the second graphical user interface: This avoids overloading of the second graphical user interface and enables the surgeon who is responsible for the eye treatment to personally have access to this critical information at all times.

Though they are generally situated at a distance to each other, the first graphical user interface displayed on the first control panel and the second graphical user interface displayed on the second control panel are in correspondence to each other via the system controller and the communication path.

The second graphical user interface is an additional graphical user interface of the laser-assisted eye treatment system, beside a first graphical user interface. It is therefore not just a copy of the first one. Additionally, the laser-assisted eye treatment system may comprise further user interfaces such as foot switches or foot control panels, mice, trackballs etc., and automatic I/O devices with I/O interfaces, the latter ones receiving information or data automatically from units of the system or from outside to system to forward it to a special unit of the system, but none of these latter user interfaces is able to control an entire workflow.

In this case, the first graphical user interface is configured to communicate a first subset of information and the second graphical user interface is configured to communicate a second subset of information out of the entire set of information required for the workflow, the first and the second subset of information being non-overlapping or partly overlapping subsets.

Non-overlapping subsets means that none of the information to be communicated out of the first subset is also part of the information to be communicated out of the second subset. Communicating an information via the first graphical user interface makes thus this same information unable to be communicated via the second graphical user interface. If, for instance, an eye treatment workflow is started on the first graphical user interface and the workflow is handed over to the second graphical user interface, there is no possibility to intervene via the first graphical user interface unless the workflow is handed back from the second graphical user interface to the first graphical user interface—either automatically, because predetermined in the workflow, or by the surgeon having finished or interrupted his part at the second graphical user interface. For this example embodiment the communication of information via the first graphical user interface or the second graphical user interface always guarantees a clear responsibility without conflicts between a person working at the first graphical user interface and the person, generally the surgeon, working at the second graphical user interface.

Partly overlapping subsets as an alternative special embodiment of the laser-assisted eye treatment system means that a part of the information out of the first subset is also part of the information out of the second subset of information. There is information that can be communicated via the first graphical user interface as well as via the second graphical user interface. This alternative embodiment may be used in situations where it is desired that an intervention by another person is possible via the first graphical user interface while the surgeon is working using the second graphical user interface to communicate information for the eye treatment workflow.

The management of the subsets may be done via the system controller.

In a further example embodiment of the laser-assisted eye treatment system the eye treatment workflow comprises several working steps corresponding to different stages of an eye treatment process. Several working steps herein means at least two or more working steps, grouping the communication of a variety of data and other information belonging to a special area of communication.

Each of the working steps is then assigned to the first graphical user interface or to the second graphical user interface. For particular working steps, an assignment to both the first and the second graphical user interface is possible: Especially a last preparation working step before handling over the command to the surgeon at the second graphical user interface might be a working step that can be accessed by the first as well as be the second graphical user interface.

The ideal workflow of a laser-assisted eye treatment system, especially of a laser-assisted eye treatment system using a pulsed laser beam, is thus advantageously designed such that most working steps are done during the non-critical sequences and fewer working steps are done during the critical sequences of a laser-assisted eye treatment process.

Using the first and the second graphical user interfaces of the laser-assisted eye treatment system during an eye treatment by a laser beam at its highest merit, a working step or simply all communication of data which is not necessarily done during the critical sequences, for instance during the laser treatment working step or during all working steps where the patient's eye is docked to the laser-assisted eye treatment system are not accessible via the second graphical user interface, but via the first graphical user interface. Vice versa, communication of information for a critical working step is not accessible via the first graphical user interface, but via the second graphical user interface, and thus always accessible to the surgeon.

In a further advantageous embodiment of the laser-assisted eye treatment system, the subset of information which the second graphical user interface is configured to communicate is defined dependent on a choice of an eye treatment process. To give an example: If the laser-assisted eye treatment system is to be used only for cataract-related treatment (i.e. laser capsulotomy and fragmentation), the subset of information displayed on the second graphical user interface will be more restricted than if the laser-assisted eye treatment system would be used for cataract surgery combined with a correction of an astigmatism. The restriction of access to the communication of information of the second graphical user interface is thus dependent on the surgery option.

For an easy handling it is further very advantageous, if the second graphical user interface of the laser-assisted eye treatment system and especially its second control panel is accessible to the surgeon who is positioned to perform microsurgery. The accessibility in said microsurgical position thus implies that the second control panel which is arranged to display the second graphical user interface is arranged next to the treatment area, i.e. less than 0.5 m away from field of surgery, for example less than 0.3 m away from field of surgery.

Advantageously, the control panel of the second graphical user interface of the laser-assisted eye treatment system comprises a small size screen, e.g. for example equal to or smaller than 13". Further it is advantageous, if the control panel of the second graphical user interface is fixed adjacent to the characterization unit and/or a laser applicator of the laser treatment unit.

In an example embodiment, the second control panel arranged to display the second graphical user interface of the laser-assisted eye treatment system is adapted to use by a surgeon in a sterile environment. For example, the second control panel is a touch screen control panel. A touch screen panel is much easier to clean and to protect from contamination than e.g. a keyboard or a mouse. For sterile operation, the second control panel can be operated through a sterile drape or using a sterile stylus.

As, in case of applying a first and a second control panel as described, it is not necessary for the first control panel to be placed such that it is visible for the surgeon, the first control panel arranged to display the first graphical user interface may comprise a large size screen. It also may be placed at a distance to the microsurgical position.

For example the size of the first control panel screen is equal to or larger than 22" to ensure that all information necessary during e.g. the preparation steps are communicated on the screen in a clearly arranged way Placing the first control panel arranged to display the first graphical user interface at a distance may require making it accessible by a network connection. Remote access may be given to the first graphical user interface, e.g., to be able to plan a laser treatment of the eye also from outside the operation room.

In an embodiment of the laser-assisted eye treatment system where the system controller—and/or the first and second user graphical user interfaces—comprises predefined settings, the first and the second graphical user interfaces are then configured to select a setting out of the predefined settings according to the required information.

As eye surgeons often practice until the age of retirement and the number of presbyopes is increasing with the age of the persons, in an example embodiment of the laser-assisted eye treatment system the first graphical user interface of first control panel and/or the second graphical user interface of the second control panel of the are configured to display information with a high level of brightness.

This means that background and any larger spatial fields of information are displayed in white or other bright colors. This is advantageous as the bright display will cause the pupils of the user to constrict, thus increasing their depth of field. This is especially advantageous for presbyopes, making it easier to clearly see the display at near distance.

This feature of displaying information entirely using bright colors may, of course, also be used independently of the laser-assisted eye treatment system for any display where a high depth of field is required and which are specially designed for presbyopes and in particular for such displays used in a difficult environment.

In a further advantageous embodiment of the laser-assisted eye treatment system, the first graphical user interface of the first control panel and/or the second graphical user interface of the second control panel is configured to display composite images. Composite images may be representations of measured eye structures and/or representations of the generated surface which are superimposed to representations of the planned eye treatment, e.g., so as to observe the success of the laser treatment of the eye compared to the planned eye treatment.

It is further preferable, for example if different categories of the composite images are periodically superimposed, to have a better visibility of the laser effects.

In another advantageous embodiment of the laser-assisted eye treatment system the images are arranged in an expand and collapse modus on the first graphical user interface of the first control panel display and/or on the second graphical user interface of the second control panel display. This allows changing the display mode between an overview mode and a detailed view mode. An image displayed on the control panel might e.g. also be a video image.

If the characterization unit scans are arranged in correct positional arrangement to an image on the first graphical user interface of the first control panel and/or on the second graphical user interface of the second control panel, this allows a better orientation for the surgeon. A characterization unit used to generate scans may be e.g. an optical coherence tomography (OCT) unit.

This graphical user interface and workflow design ensures high efficiency, especially during the critical docking phase of the procedure, and reduces the risk of mistakes.

The problem is further solved by a method for generating control data for a laser-assisted eye treatment system. Generating control data for a laser-assisted eye treatment system means determining all data necessary to control a specific treatment of a patient's eye by the laser-assisted eye treatment system.

The control data for the laser-assisted eye treatment system comprise an eye treatment pattern. Such an eye treatment pattern includes all information on the position or the positions where an eye treatment has to be carried out, but it may also include information on laser parameters for each concrete position, like e.g. beam intensity of the laser beam or pulse repetition rate when using a pulsed laser beam.

According to the invention, the eye treatment pattern is planned, and thus the respective control data is generated, fundamentally based on the definition of an anatomy of the patient's eye. It is not possible to directly modify the eye treatment pattern, e.g. by directly providing information on a desired position of the eye treatment pattern.

The eye treatment pattern is always a result of the concrete anatomy of a patient's eye, for example, corrected by secondary effects like interactions between different treatment patterns or deformations during the eye treatment.

In the most common case of an eye treatment pattern generation, an automatic pattern generation of incisions into an eye tissue of the patient's eye by photodisruption, induced by a pulsed laser beam, is based on the definition of the anatomy of the eye.

In an advantageous embodiment of the method for generating control data, an eye treatment pattern is planned strictly in relation to a clinical objective and an ideal anatomical structure, e.g. using a virtual model eye. This eye treatment pattern is remapped and reviewed strictly in relation to a detected real anatomical structure, which may imply to be modified, after defining the anatomy of the patient's eye.

The definition of the anatomy of the patient's eye may be done based on a characterization of the patient's eye prior to the eye treatment or during an eye treatment.

Alternatively, an eye treatment pattern based on any anatomy of an eye is remapped and reviewed after defining the anatomy of the patient's eye strictly in relation to a detected real anatomical structure.

In a further embodiment of the method for generating control data, the eye treatment pattern is corrected by effects related to a docking of the patient's eye to the laser-assisted eye treatment system and/or by effects related to interactions between different treatment patterns and/or to movements of the eye and/or to an individual variance of the patient's eye.

The docking of the patient's eye to a laser-assisted eye treatment system leads to a pressure on the patient's eye and thus to a deformation of the anatomical structure of the patient's eye due to this pressure. The eye often being treated while docked to the laser-assisted eye treatment system, it is very advantageous to directly take into account this deformation for the generation of the control data and especially for planning the eye treatment pattern.

On the other hand, a first eye treatment pattern may have an influence on a second eye treatment pattern, as the execution of the first eye treatment pattern, especially for incisions, influences the real anatomic structure of the eye and has to be considered for the second eye treatment pattern and vice versa.

Also the patient's eye may present an individual variance. Further, movements of the patient's eye—if not prevented—should be considered.

For example, the method for generating control data is used to control a laser-assisted eye treatment system as described above by application of the generated control data.

The problem is further solved by a planning method for a laser-assisted eye treatment of a patient's eye. A planning method for a laser-assisted eye treatment of a patient's eye comprises all steps of preparation of a laser-assisted eye treatment before starting the laser-assisted eye treatment itself.

According to the invention, the eye treatment is planned fundamentally based on the definition of an anatomy of the patient's eye.

To plan the eye treatment fundamentally based on the definition of an anatomy of the patient's eye means that there is no "direct planning" of the eye treatment, as it is not possible to directly design, edit or move an eye treatment pattern e.g. on a graphical user interface of an laser-assisted eye treatment system or manually directly enter a position of an eye treatment pattern. The eye treatment and especially the eye treatment pattern is therefore always a result of the concrete anatomy of a patient's eye, for example corrected by secondary effects like interactions, individual variance, movements or deformations during the eye treatment. For editing the eye treatment pattern, the anatomy of the eye has to be reviewed.

In an example embodiment of the planning method, a planning of the eye treatment is done strictly in relation to a clinical objective and to an ideal anatomical structure of a virtual model eye. The planning of the eye treatment is remapped and reviewed after defining the real anatomy of the patient's eye strictly in relation to a detected real anatomical structure.

The definition of the anatomy of the patient's eye may be done based on the data of a characterization of the patient's eye prior to the eye treatment or during an eye treatment.

Alternatively, a planning of the eye treatment based on any anatomy of an eye is then remapped and reviewed after defining the anatomy of the patient's eye strictly in relation to a detected real anatomical structure.

For example, the planning of the eye treatment is started in reference to an ideal anatomic model of the eye, and a step of defining an anatomy of the patient's eye is followed by an automatic pattern generation of the eye treatment pattern, e.g. in case of cataract surgery being incisions, based on the definition of the anatomy of the eye. If the surgeon feels that he or she should correct the treatment pattern, he or she will do it by correcting the definition of the anatomy. The surgeon thus does not shift the position of a treatment pattern, e.g. of an incision, but always intervenes on the definition of the anatomy, which automatically determines the position of the treatment pattern. If the surgeon is satisfied, he only approves the proposed generated pattern of the eye treatment.

During the review of the planning, the planning of the eye treatment is adapted—if necessary—according to the results of the definition of the anatomy of the patient's eye.

In a further embodiment of the planning method the planning of the eye treatment is corrected by secondary effects, e.g. effects related to a docking of the patient's eye to the laser-assisted eye treatment system, to interactions between different treatment patterns, individual variance and/or movements.

The problem is further solved by an eye treatment method using a laser beam, for example a pulsed laser beam, for treating a patient's eye.

An eye treatment method as understood here is a method for treating eye tissue, which may for example be the cornea, the limbus, the pupil or the lens, including the lens capsular membrane. It also may be another material, including an artificial material in a patient's eye.

An eye treatment method using a laser beam may result in an effect of cutting, e.g. by photodisruption using a focused pulsed laser beam. It may result in an effect of "bonding" or another modification of the eye tissue by coagulation. Further it may result in a shaping effect using laser ablation.

According to the invention, the eye treatment method comprises a planning method as described above. This means, that the eye treatment method comprises a planning method wherein the eye treatment is planned fundamentally based on the definition of an anatomy of the patient's eye.

This eye treatment method avoids resulting additional errors that may appear, if the surgeon or another user has the possibility to freely intervene on an eye treatment by freely editing an eye treatment pattern, especially an incision pattern.

For example, the eye treatment method makes use of a laser-assisted eye treatment system as described above.

Therefore the system controller of the laser-assisted eye treatment system may be encoded to carry out the described eye treatment method. Particularly, the system controller may be encoded to provide the relevant first and/or second graphical user interface to the first and/or second control panel for each of the working steps.

The system controller might especially comprise a planning unit, which is encoded by a routine for planning the eye treatment strictly based on an anatomy of a patient's eye and taking over the generation of control data for a laser-assisted eye treatment system. This planning unit might be an integrated part of the system controller taking over the planning functions described—especially of a single part system controller. It also might be a locally separated unit—being part of a system controller comprising several parts as described above.

In a further example embodiment, the eye treatment method using a laser beam for treating a patient's eye is following a workflow comprising the working steps of:
  selecting a patient,
  planning the eye treatment using a virtual model eye,
  defining an anatomy of the patient's eye,
  remapping and reviewing the planning of the laser treatment, and
  applying a laser treatment to the eye.

In an advantageous embodiment of the eye treatment method, the workflow further comprises the working steps of docking the patient's eye to a laser-assisted eye treatment system, for example before defining an anatomy of the patient's eye, and undocking the patient's eye from the laser-assisted eye treatment system for example after the laser treatment. The information required for these working steps may be communicated via the second graphical user interface.

The docking of the patient's eye to the laser-assisted eye treatment system is the starting point of a critical phase of the eye treatment because of potential damages that might be caused to the eye during that phase. It is evident that performing the eye treatment planning on a virtual model eye, in a special embodiment even already refined using characterization data of the patient's eye acquired by a separate external pre-treatment characterization session, considerably shortens this critical phase of the eye treatment.

For example, the eye treatment method is characterized in that the information required for the working step of selecting a patient is communicated via a first graphical user interface. In this working step, it is possible either to select a concrete patient's name and thus to load all data registered for this patient, or to select an "anonymous patient" to start an eye treatment routine without loading personalized data.

Further, according to the invention, the information required for the working step of planning the eye treatment is communicated via a first and/or a second graphical user interface. The planning of the eye treatment is done on a virtual model eye.

Last but not least, the information required for the working steps of defining the anatomy of the patient's eye, reviewing the planning and executing the laser treatment is communicated via a second graphical user interface. This second graphical user interface displayed on a second control panel may have an easy and comprehensible structure, as it serves only for particular steps requiring a lower amount and especially a lower variety of information to be communicated. That is why the second control panel may be smaller than the first control panel displaying the first graphical user interface. Therefore the second control panel displaying the second graphical user interface may be disposed next to the surgeon. Thus the surgeon can personally control the eye treatment using this second graphical user interface.

The workflow may further comprise the working step of reporting after the laser treatment, which is generally done after the undocking if the docking and undocking steps are done, wherein the information required is communicated via the first graphical user interface.

Finally the workflow of the eye treatment method may further comprise the working step of planning the eye treatment, e.g., incisions into an eye tissue or other modifications of an eye tissue by the laser beam, wherein the information required is communicated via the first and/or the second graphical user interface.

The laser-assisted eye treatment system as well as the eye treatment method using a laser beam according to the invention allows a surgeon or other staff member to choose among quite different modes of an eye treatment, all of them operating safely and autonomously, especially during the critical sequences, proposing to the surgeon and other staff members a simple comprehensible and intuitive structure of a workflow.

The laser-assisted eye treatment system as well as the eye treatment method using a laser beam according to the invention is easily operable in a sterile environment, and actively avoid accidents arising from maloperation by the surgeon or another person handling the system.

As the workflow is clearly structured and the critical working steps as well as their content are reduced to the absolute minimum, it further helps to shorten a possible docking time of the eye to be treated to the laser-assisted eye treatment system.

BRIEF DESCRIPTION OF THE DRAWINGS

Features and advantages of the present invention and its modes of operation as well as advantageous combinations of different features will become more apparent considering the following detailed description and embodiments with reference to the accompanying drawings.

DETAILED DESCRIPTION

Figure 1:
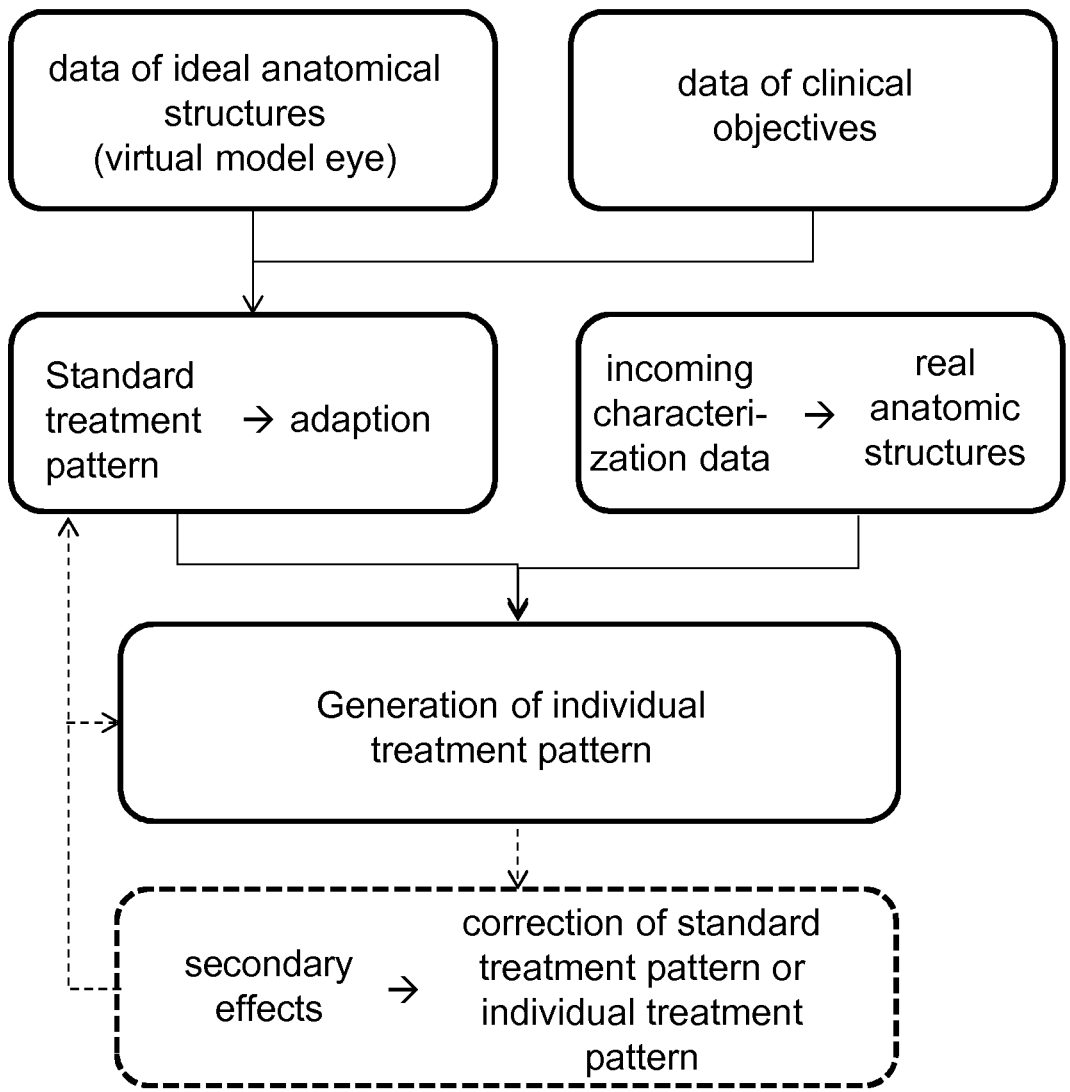
FIG. 1 gives an overview of an embodiment of the computer program product according to the invention.

FIG. 1 gives an overview of an embodiment of the computer program product according to the invention. It illustrates the interactions between different sections of the computer program product.

There are sections for storing data of ideal anatomical structures, e.g. the anatomical structures of a virtual model eye, and clinical objectives. Having chosen the most appropriate structure and/or objective among these data, the chosen data are used to adapt a standard treatment pattern in a corresponding section.

Using incoming or detected characterization data, the real anatomic structures are determined in a further section. By help of these determined real anatomic structures and the adapted standard treatment pattern, an individual treatment pattern is generated in the following section.

The standard treatment pattern or the generated individual treatment pattern may further be corrected by secondary effects in an optional section. Examples for such secondary effects are effects related to a docking of the patient's eye to the laser-assisted eye treatment system, to interactions between different treatment patterns, to an individual variance and/or to movements of the patient's eye.

Figure 2:
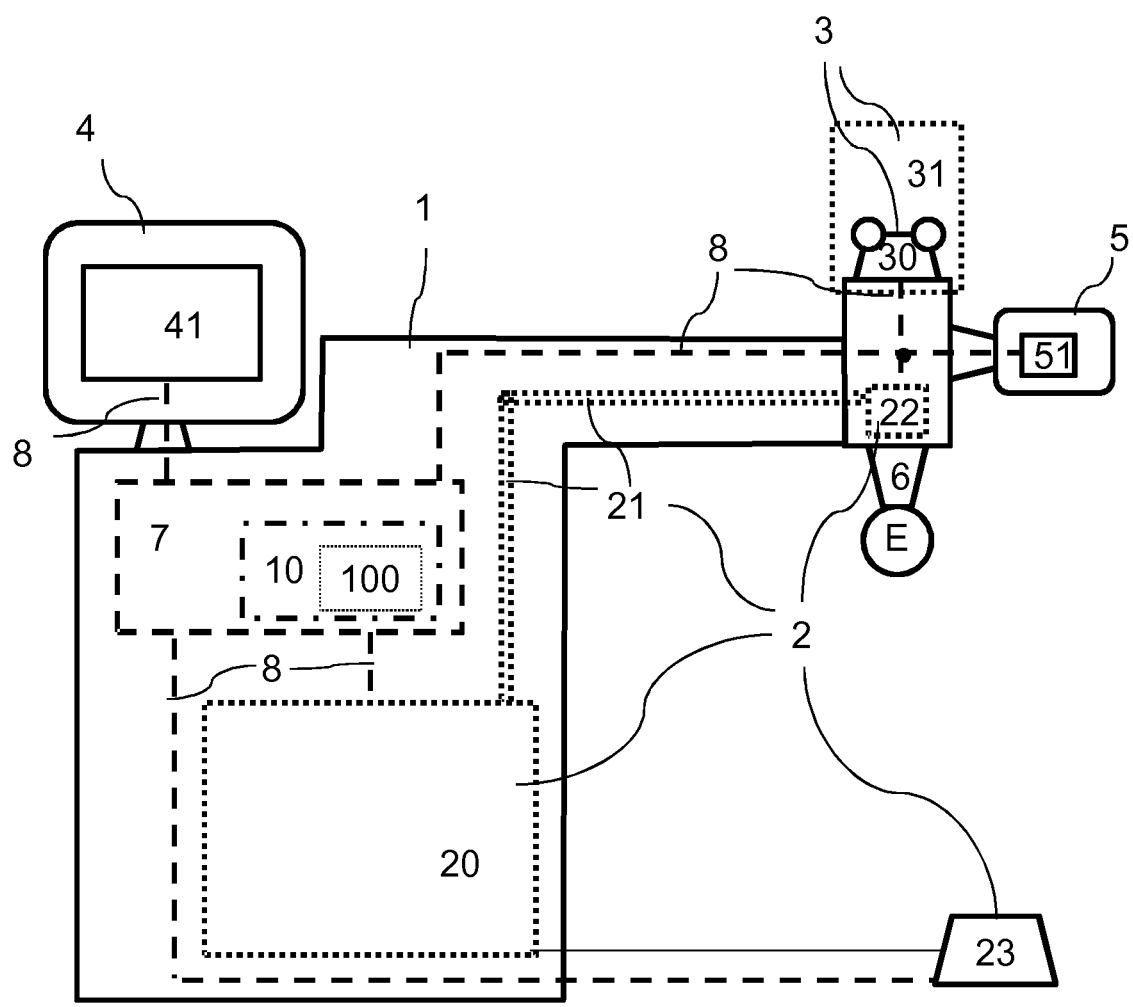
FIG. 2 shows a scheme of different features and their relationship of an embodiment of the laser-assisted eye treatment system.

FIG. 2 shows a scheme of an example of a laser-assisted eye treatment system 1 according to the invention, especially explaining its substructure and different features and the relationship between the different features.

A laser-assisted eye treatment system 1 is configured to carry out an eye treatment workflow. It comprises a laser treatment unit 2, which includes a laser console 20, a laser guiding system 21, a laser applicator 22 and a laser foot switch 23. The laser console 20 also comprises the laser source, i.e. it generates a pulsed laser beam. For the example of FIG. 2 it comprises a femtosecond laser source, generating a pulsed femtosecond laser beam.

The laser guiding system 21 deflects the laser beam in a flexible manner. It is movable for placing the laser applicator 22, which is following at the further end of the laser guiding system 21, at the required position over a patient's eye E. The patient, not shown in FIG. 2, may be placed on an operation bed, in an horizontal position beside the laser-assisted eye treatment system 1. The flexible laser guiding system 21, which allows to move the laser applicator 22 within a three-dimensional space along three directions, is then actuated to adjust to position of the laser applicator 22 exactly over the eye E of the patient. Alternatively, the patient may be placed in the position directly below the laser applicator 22.

To focus the laser beam to an eye E, the laser applicator 22 of the laser treatment unit 2 comprises a focusing optics (not shown in FIG. 2). An three dimensional focus shifting system is further comprised in the laser treatment unit 2—for the example of FIG. 2 it is part of the laser guiding system 21 and/or the laser applicator 22. It is realized by a x-y scanner system and an additional z scanner system (not shown in FIG. 2).

Using a patient interface 6, the patient's eye may then be docked to the laser-assisted eye treatment system 1.

The laser foot switch 23 of the example is used to command the action of the pulsed laser beam. Especially in case of emergency, such an additional user interface is very useful, as it offers the shortest way to interrupt the laser beam.

The laser-assisted eye treatment system 1 further comprises a characterization unit 3. For the present example the characterization unit 3 comprises an operation microscope system 30 and an OCT (optical coherence tomography) system 31, which are not displayed in detail in FIG. 2, allowing a permanent and detailed observation of the eye region to be treated. In particular, the OCT system 31 is providing the imaging of the patient's eye E which is necessary to detect the anatomical structures of the eye E.

A system controller 7 is configured to control the laser-assisted eye treatment system 1. The system controller 7 is coupled to the respective features of the laser-assisted eye treatment system 1 via communication paths 8. The system controller 7 comprises a memory section, where a computer program product 100 is stored, which is configured to encode a system controller 7 for example of a laser-assisted eye treatment system 1 by a routine for planning the eye treatment strictly based on an anatomy of a patient's eye E.

The computer program product 100 is further configured to encode the system controller 7 by a routine for a planning of the eye treatment strictly in relation to a clinical objective and to an ideal anatomical structure and for a remapped and reviewed planning of the eye treatment strictly in relation to a detected real anatomical structure of the patient's eye E.

As the patient's eye E is docked to the laser-assisted eye treatment system 1, the computer program product 100 is further configured to encode the system controller 7 by a routine for correcting the planning of the eye treatment by effects related to a docking of the patient's eye E to the laser-assisted eye treatment system 1. Within the system controller 7, a planning unit 10 is localized—being an integrated part of this system controller 7. This planning unit 10 is encoded by a routine for planning the eye treatment strictly based on an anatomy of a patient's eye. It is taking over the generation of control data for a laser-assisted eye treatment system within the system controller 7, Further, the computer program product 100 is configured to encode the system controller 7 by a routine for correcting the planning of the eye treatment by effects related to an interaction between different treatment patterns, to an individual variance or to movements of the patient's eye.

The laser-assisted eye treatment system 1 further comprises a first control panel 4 displaying a first graphical user interface 41 which is provided by the system controller 7 via a communication path 8.

The laser-assisted eye treatment system 1 further comprises a second control panel 5 displaying a second graphical user interface which is provided by the system controller 7 to this second control panel 5. This second graphical user interface 51 is configured to communicate a subset of information out of an entire set of information required for the eye treatment workflow, notably to communicate a subset used during the critical working steps of the eye treatment using the pulsed femtosecond laser beam to cut eye tissue in this case. The second control panel 5 displaying the second graphical user interface 51 is arranged near to the micro-surgery position, thus being easily accessible by the surgeon carrying the laser treatment of the patient's eye E.

The surgeon can thus use of the second graphical user interface 51, which displays the information of the subset in a clear and structured way, to check the results of the detection of the anatomical structures of the eye E, which are provided by the imaging of the patient's eye E by help of the OCT system 31, and to check the proposed treatment pattern, which are planned strictly based on the detected anatomy by the routine the system controller 7 is encoded with by the computer program product 100. The surgeon can further intervene when he considers that a modification is required by reviewing the detected anatomical structures of the eye E.

Once the proposed treatment pattern is confirmed, the surgeon starts the laser treatment of the eye using this treatment pattern strictly based on the real anatomical structures of the patient's eye E.

Figure 3:
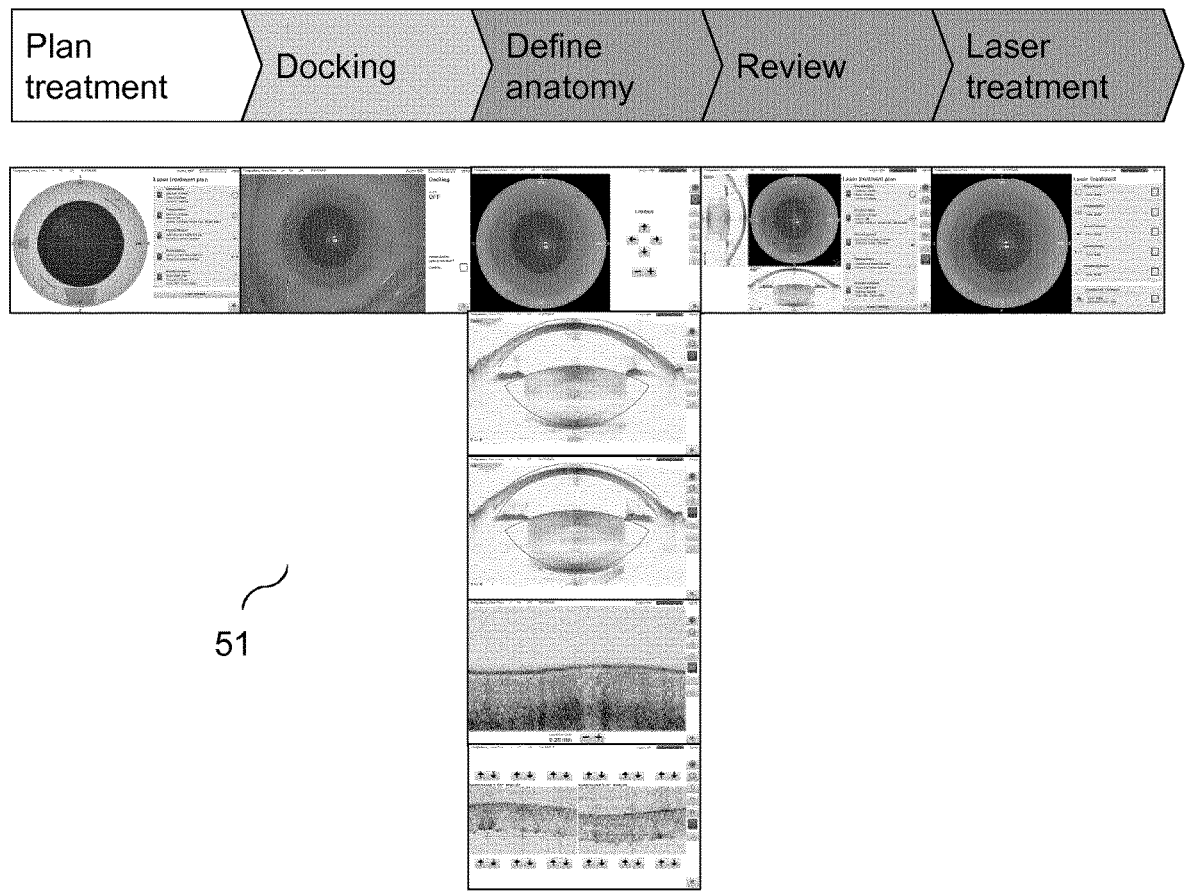
FIG. 3 is a detailed view of a control panel screen of a laser-assisted eye treatment system displaying a graphical user interface displaying working steps of an encoded workflow.

FIG. 3 is a detailed view of a graphical user interface, especially of a second graphical user interface 51 of a second control panel screen 5 of a laser-assisted eye treatment system. It illustrates the arrangement of images in an expand and collapse modus on this second graphical user interface of the second control panel screen 5, following a workflow for the laser-assisted eye treatment encoded in the laser-assisted eye treatment system, comprising different working steps, especially the working steps:

plan treatment
docking
define anatomy
(remap and) review
laser treatment

FIG. 3 also illustrates the application of the laser-assisted eye treatment method to generate laser incisions in an eye tissue of a patient's eye.

As a part of the laser-assisted eye treatment method, but alternatively also as an independent method for generation of control data and/or as an independent planning method for a laser-assisted eye treatment of a patient's eye it comprises the following steps:

The spatial position planning of the laser incisions is done in a "Plan treatment" step strictly based in clinical objectives and in relation to ideal anatomical structures, following the relationships given in table 1.

After having docked a patient's eye to the laser-assisted eye treatment system, an imaging of the patient's eye is performed to define the anatomy of the patient's eye. The detected data may be checked and corrected, then the detection of anatomical structures is confirmed. In this example, the anatomy is defined by optical coherence tomography (OCT) unit scans, the OCT unit being part of the laser-assisted eye treatment system.

Alternatively, the anatomical structures of the patient's eye may be defined prior to the laser-assisted eye treatment, the detected data may be used for the calculation.

The absolute spatial position of the incisions is then automatically calculated relative to these anatomical structures. In the review phase, the surgeon can view and confirm the absolute spatial position of the incisions. If corrections are needed, the surgeon can correct the detection of the anatomical surfaces or correct parameters which define the incisions in relation to the anatomical structures. It is not possible to directly manipulate the absolute position of the laser incisions.

Tab. 1 illustrates the dependence of eye treatment parameters, especially of the incision parameters, on the anatomical parameters and on clinical objectives for different incision types.

All incision parameters are based on at least one of the following:
a clinical objective,
a position relative to an anatomical structure,
a position relative to one or more other incisions.

FIG. 4*a*-4*d* show a first example for a planning method for a laser-assisted eye treatment and for generating control data for a laser-assisted eye treatment system: It illustrated the planning of a capsulotomy by a laser-assisted eye treatment by help of a graphical user interface 51 of a control panel 5 of a laser-assisted eye treatment system 1.

Figure 4A:
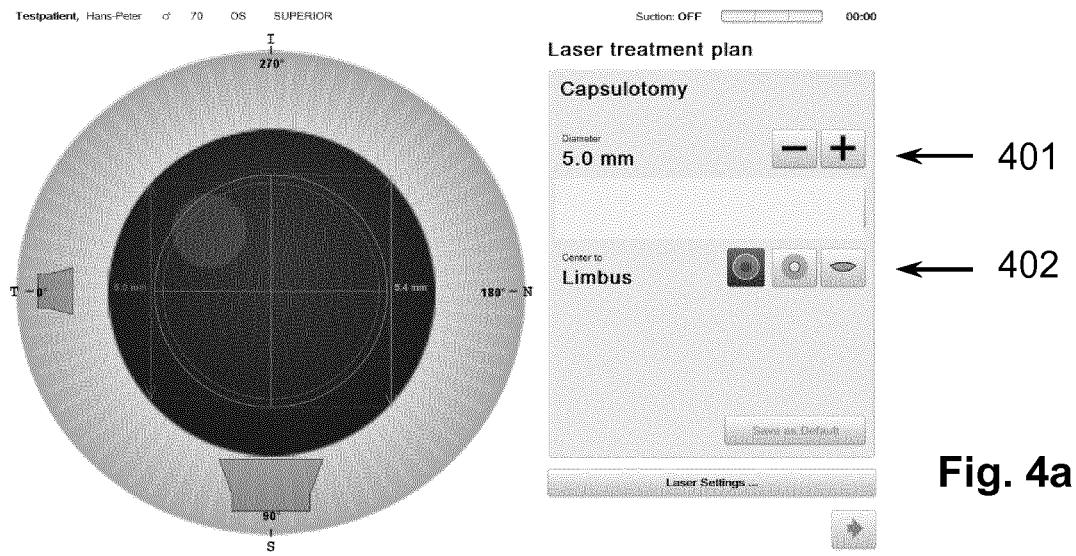
FIG. 4a-4d show a first example for a planning method for a laser-assisted eye treatment and for generating control data for a laser-assisted eye treatment system.

At position 401 of FIG. 4*a*, the diameter of the capsulotomy is a clinical objective determined by the surgeon. At position 402, the capsulotomy can be centered to the limbus, to the pupil or to the lens shape.

Figure 4B:
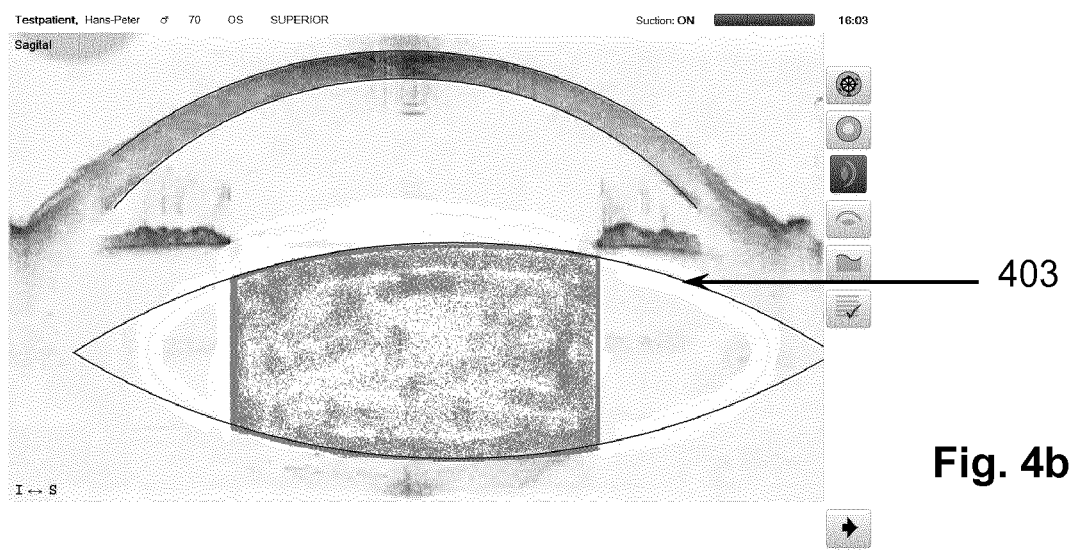

After imaging, e.g. by the OCT system 31, the surgeon confirms and corrects the detection of the anterior capsular membrane at position 403 of FIG. 4b.

Figure 4C:
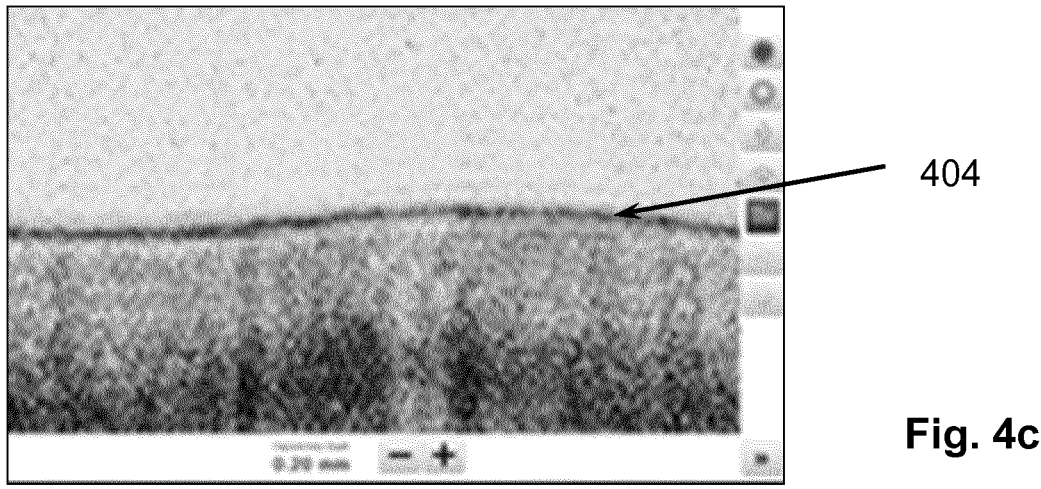

At position 404 of FIG. 4c, a final correction to account for surface irregularity is done on the basis of a circular scan of the anterior capsular membrane.

Figure 4D:
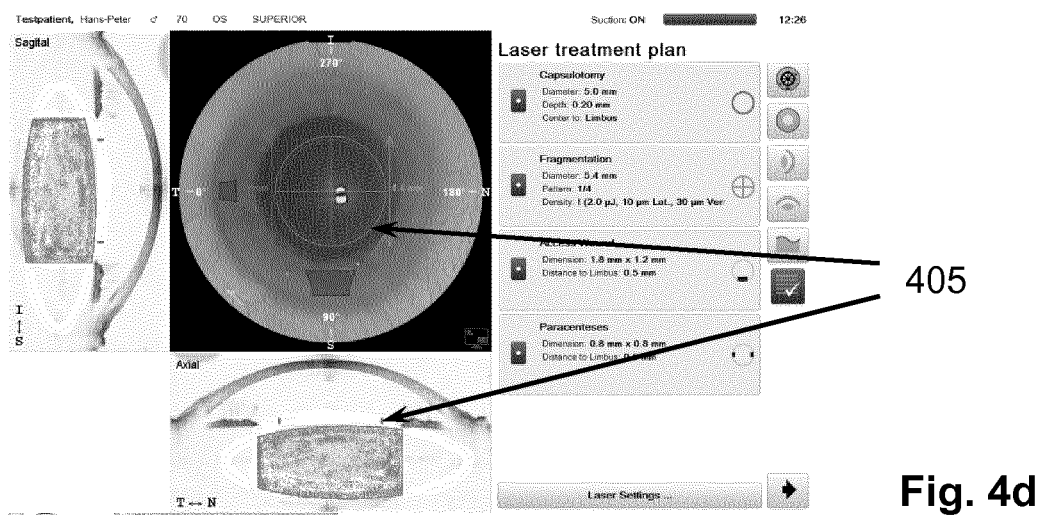

At position 405 of FIG. 4d, the absolute spatial position of the capsulotomy is shown in the final review screen.

Figure 5A:
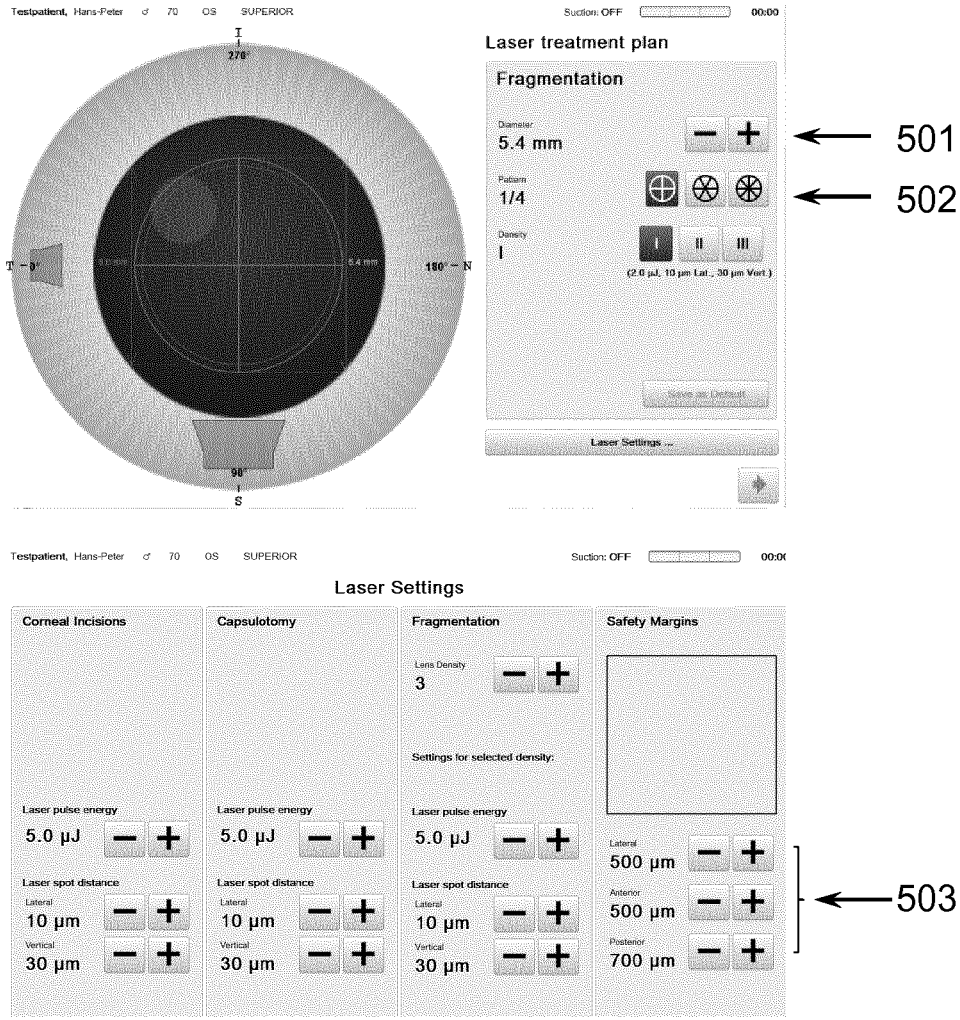
FIG. 5a-5c show a second example for a planning method for a laser-assisted eye treatment and for generating control data for a laser-assisted eye treatment system.
Figure 5B:
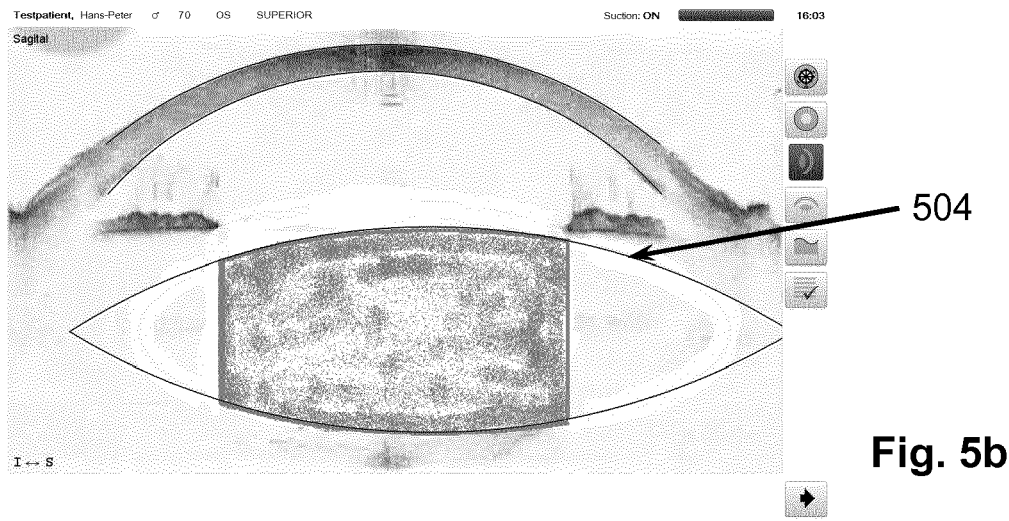
Figure 5C:
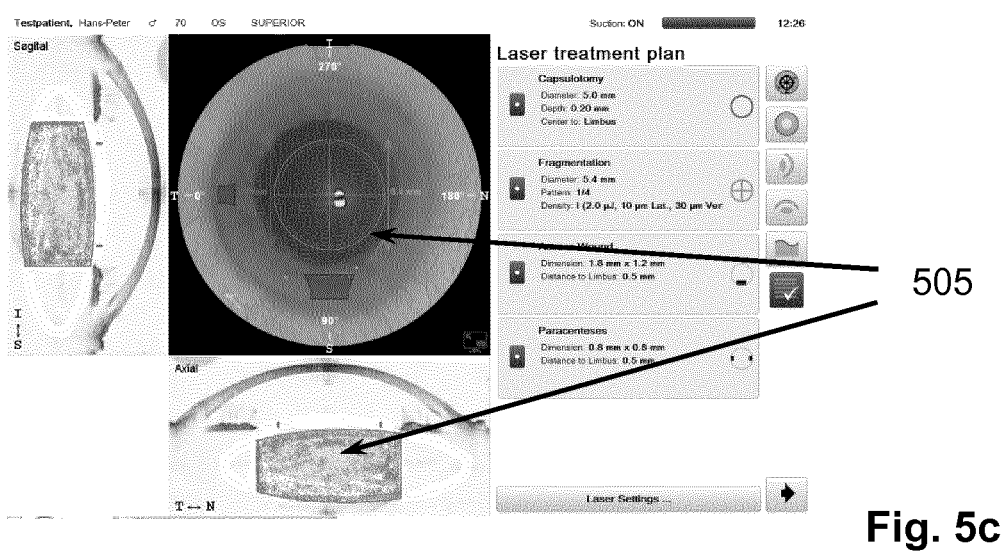

FIG. 5a-5c show a second example for a planning method for a laser-assisted eye treatment and for generating control data for a laser-assisted eye treatment system: It illustrated the planning of a lens fragmentation by a laser-assisted eye treatment by help of a graphical user interface 51 of a control panel 5 of a laser-assisted eye treatment system 1.

At position 501 of FIG. 5a the diameter of the lens fragmentation is chosen by the surgeon. The diameter of the fragmentation is a clinical objective: Clinical objectives are only indirectly dependent of the anatomical structures. The diameter has to be within the safety zones for not injuring the capsular membranes. The lens fragmentation is then automatically centered to the capsulotomy. The pattern chosen at position 502 is a clinical objective.

At position 503, the anterior and posterior incision depth and thus the treatment depth is determined by the safety zones relative to the anterior and posterior capsular membranes.

After docking, the surgeon needs only to correct and confirm the detection of the anatomy as shown in position 504 of FIG. 5b.

At position 505 of FIG. 5c, the absolute spatial position of the lens fragmentation is shown in the final review screen.

Figure 6:
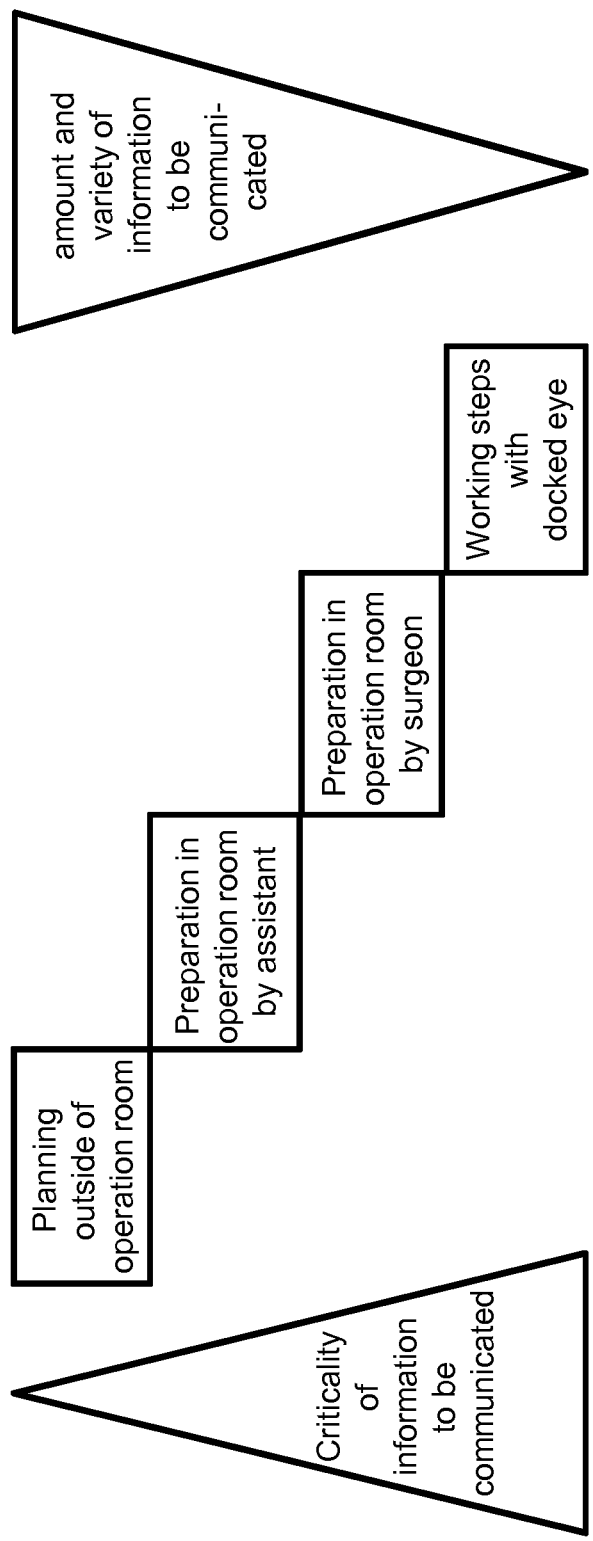
FIG. 6 shows the criticality as well as the amount and variety of information to be communicated during an eye treatment as already mentioned above.

As already mentioned, FIG. 6 shows the criticality as well the amount and variety of information to be communicated during an eye treatment the laser-assisted eye treatment system 1 set-up is considering.

The planning of an eye treatment by a laser-assisted eye treatment system 1 may be done at any time and also outside the operation room. It is requiring a large amount and variety of information to be communicated, but the information is not time critical and a given wrong item of information may be corrected.

The first part of the preparation of an eye treatment by a laser-assisted eye treatment system 1 is generally done in the operation room, but not by the surgeon himself, but by an assistant. Even the preparation steps are not time critical and wrong information may still be corrected.

The final part of the preparation of an eye treatment by a laser-assisted eye treatment system 1 is necessarily done in the operation room by the surgeon himself, just prior to the laser treatment. The communicated information are already critical, as there is no further "control instance" prior to the eye treatment.

Finally, information to be communicated during all eye treatment working steps, or, if the eye to be treated is docked to the laser-assisted eye treatment system 1, all working steps with docked eye E, is very critical information. Wrong information can cause immediate and non-reversible damage of the eye E.

Figure 7:
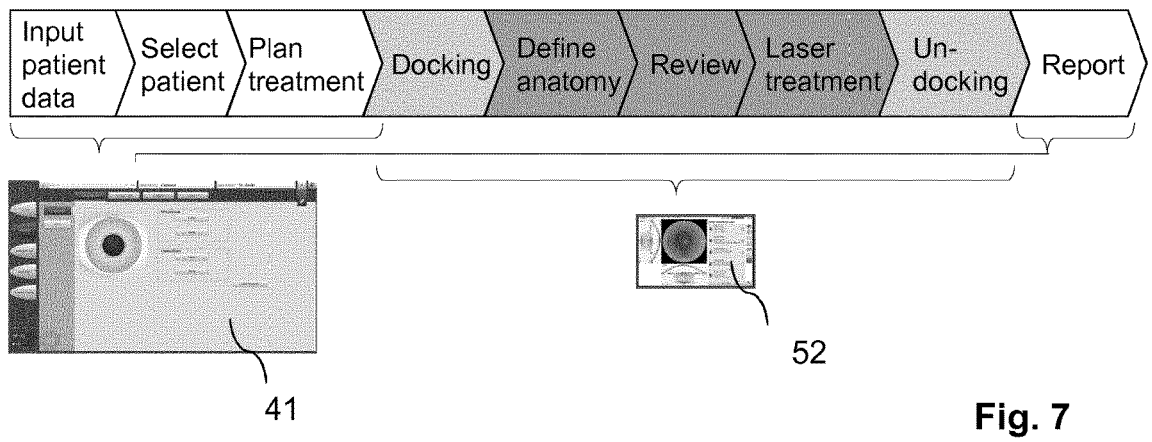
FIG. 7 shows possibilities of working steps repartitions as well as exemplary first and second control panel screens of first and second graphical user interfaces—as a special embodiment of the "eye treatment planning strictly based on the anatomy of the eye", especially of a laser-assisted eye treatment system which is encoded that way. But this kind of working steps repartition may also be used independently of the "eye treatment planning strictly based on the anatomy of the eye" idea. Nevertheless, it is most helpful used together with the eye treatment planning which is carried out strictly based on the anatomy of the eye.

FIG. 7 shows possibilities of working steps repartitions between the first graphical user interface 41 and a second graphical user interface 51, as well as a first control panel screen 4 displaying an exemplary first graphical user interface 41 and a second control panel screen 5 displaying an exemplary second graphical user interface 51.

Within this exemplary working steps repartition, at least the working steps of defining anatomy, reviewing and laser treatment have to be done while docking the eye E to the laser-assisted eye treatment system 1.

Figure 8:
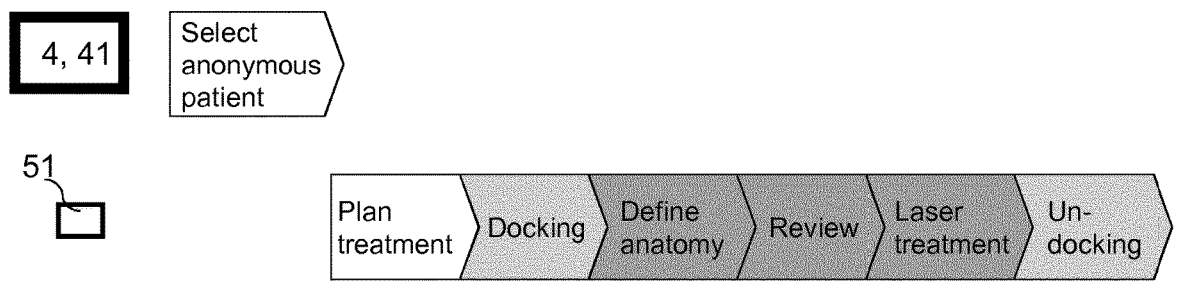
FIG. 8 shows a first embodiment of a working steps repartition between first and second graphical user interface for a first eye treatment workflow.

FIG. 8 shows a first embodiment of a working steps repartition between first 41 and second graphical user interface 51 for a first eye treatment workflow. It is an exemplary workflow for an eye treatment without entering or storing patient data. In this case it is possible for the surgeon to plan and perform the key functions of the entire laser procedure without entering patient data such as name, birthday, etc.

The surgeon or a staff member only creates or selects an anonymous patient and then presses "start procedure" on the large control panel screen 4 displaying the first graphical user interface 41.

Everything else—including treatment planning—can then be done on the small control panel screen 5 displaying the second graphical user interface 51. On the second graphical user interface 51 of this small screen 5, the surgeon thus plans the treatment, docks on the eye E, performs imaging, defines anatomy, does final review, and starts the laser.

Figure 9:
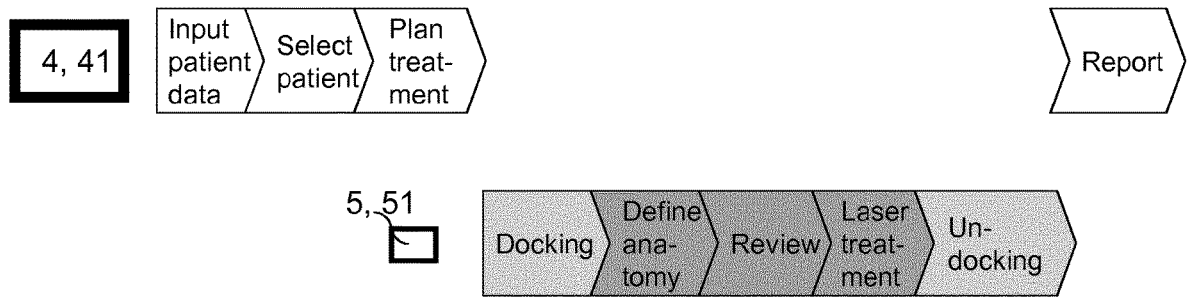
FIG. 9 shows a second embodiment of a working steps repartition between first and second graphical user interface for a second eye treatment workflow.

FIG. 9 shows a second embodiment of a working steps repartition between first graphical user interface 41 and second graphical user interface 51 for a second eye treatment workflow. It is a workflow for an eye treatment storing patient data. The entering of the patient data—for one or more patients at once—, the selection of a patient and the planning of the treatment of the selected patient is done using the first graphical user interface 41 of the large control panel screen 4. This might be done by the surgeon or by a staff member based on instructions from the surgeon. Then the procedure is started on the first graphical user interface 41 of the large control panel screen 4.

All other steps are done by the surgeon using the second graphical user interface 51 of the small control panel screen 5 after the procedure has been started. On the second graphical user interface of the small control panel screen 5, the surgeon thus reviews the planning, docks on the eye E, performs the imaging, defines the anatomy, does a final review, and starts the laser for the laser treatment of the eye E, further observes and, if necessary, corrects the laser treatment.

A final report of the achieved laser treatment is then done after the undocking of the eye E, which was initiated on the second graphical user interface 51 of the small control panel screen 5, on the first graphical user interface 41 of the large control panel screen 4. This reporting may be done by the surgeon or by a staff member again based on the instructions from the surgeon.

Figure 10:
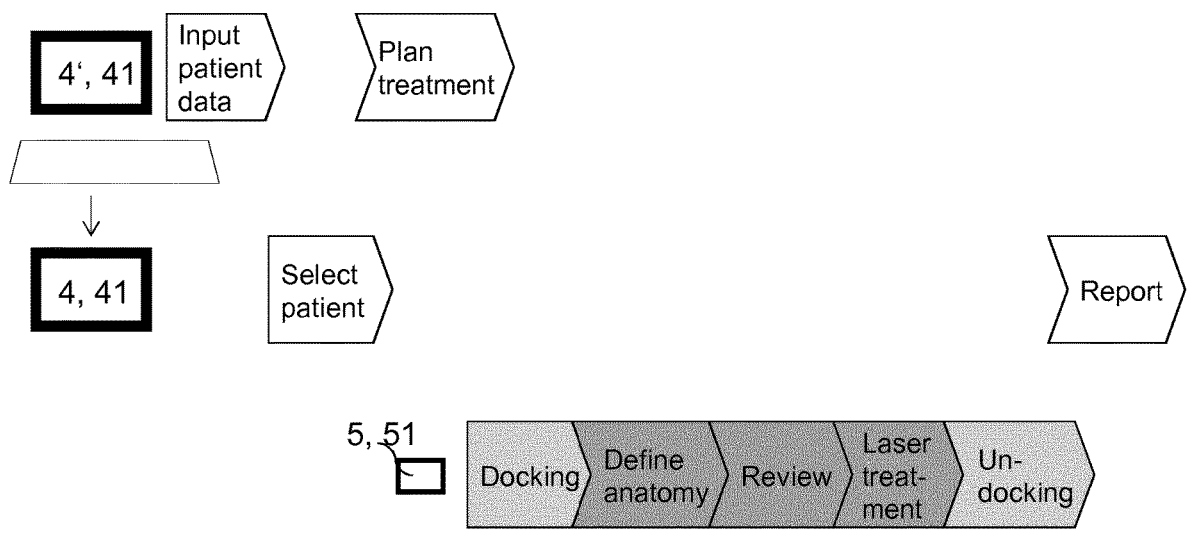
FIG. 10 shows a third embodiment of a working steps repartition between first and second graphical user interface for a third eye treatment workflow.

FIG. 10 shows a third embodiment of a working steps repartition between first 41 and second graphical user interface 51 for a third eye treatment workflow. It is another workflow for an eye treatment storing patient data.

In this case, the patient data may be entered and the procedure planned on a system located outside of the operation room—either by the surgeon or by a staff member based on instructions from the surgeon—on a network personal computer by remote access to the first graphical user interface 41 via a network connection.

The data is thus imported to the system in the operation room via the network connection. The surgeon or a staff member then selects the patient on the first graphical user interface of the large control panel screen 4 and presses "start procedure".

On the second graphical user interface of the small control panel screen 5, the surgeon reviews the planning, docks on the eye E, performs the imaging, defines the anatomy, does a final review, and starts the laser treatment of the eye E, further observes and, if necessary, corrects the laser treatment.

Again, a final report of the achieved laser treatment is then done on the first graphical user interface 41 of the large control panel screen 4 after the undocking of the eye E, which was initiated on the second graphical user interface 51 of the small control panel screen 5. This reporting may be done by the surgeon or by a staff member again based on the instructions from the surgeon.

The features of the invention mentioned above and explained in several embodiments are not only applicable in the combinations explained in the exemplary embodiments, but also in other combinations or alone without exceeding the scope of the present invention.

A feature related to and characterized for the system applies in analogy to the relevant method, while method features may be applied as functional features of the system described accordingly.

The invention claimed is:

1. A laser-assisted eye treatment system that carries out an eye treatment workflow, the system comprising:
    a laser treatment unit with a laser source generating a laser beam;
    a focusing optics and a three dimensional focus shifting system;
    a system controller, configured to control the laser-assisted eye treatment system;
    a predefined virtual model eye representing an ideal anatomical structure stored by the system controller;
    wherein the system controller is encoded with a computer program comprising instructions configured to encode the system with a routine, the routine comprising:
    prior to a critical phase of the eye treatment, planning the eye treatment strictly in relation to a clinical objective and to the ideal anatomical structure of the predefined virtual model eye;
    detecting a real anatomical structure of the patient's eye by imaging the patient's eye by use of a characterization unit; and
    remapping and reviewing the planned eye treatment strictly in relation to the detected real anatomical structure of the patient's eye.

2. The laser-assisted eye treatment system according to claim 1, further comprising a first control panel arranged to display a first graphical user interface provided by the system controller and configured to communicate information required for the eye treatment workflow.

3. The laser-assisted eye treatment system according to claim 2, further comprising a second control panel arranged to display a second graphical user interface provided by the system controller and configured to communicate a subset of information out of an entire set of information required for the eye treatment workflow.

4. The laser-assisted eye treatment system according to claim 3, wherein the first graphical user interface of the first control panel the second graphical user interface of the second control panel or both is configured to display composite images.

5. The laser-assisted eye treatment system according to claim 3, wherein different categories of the composite images are periodically superimposed.

6. The laser-assisted eye treatment system according to claim 1, wherein the laser source generates a pulsed laser beam.

7. The laser-assisted eye treatment system according to claim 1, wherein the instructions are further configured to encode the system controller with the routine comprising:
    correcting the planning of the eye treatment by secondary effects related to a docking of the patient's eye to the laser-assisted eye treatment system, effects related to an interaction between different treatment patterns, effects related to movements, effects related to individual variance or a combination of the foregoing.

8. The laser-assisted eye treatment system according to claim 1, the instructions further comprising
    a section that stores data on at least an ideal anatomical structure, a section for storing at least a clinical objective;
    a section for storing and adapting standard treatment patterns;
    a section for treating and storing incoming characterization data for establishing real anatomical structures; and
    a section for generating an individual treatment pattern.

9. The laser-assisted eye treatment system according to claim 1, the instructions further comprising a section for correcting the standard treatment pattern or the individual treatment pattern by secondary effects.

10. The laser-assisted eye treatment system according to claim 1, further comprising the characterization unit.

11. The laser-assisted eye treatment system according to claim 1, further wherein an eye treatment workflow is encoded in the system controller comprising:
    planning the treatment
    defining anatomy of the patient's eye
    reviewing the planning
    laser treatment according to the planning.

12. The laser-assisted eye treatment system according to claim 1, further comprising:
    a docking unit arranged to establish a defined relationship between the laser-assisted eye treatment system and a patient's eye to be treated; and wherein the eye treatment workflow encoded in the system controller further comprises docking of the patient's eye to the laser-assisted eye treatment system before the defining the anatomy.

13. The laser-assisted eye treatment system according to claim 1, wherein the system controller comprises predefined settings that are categorized.

14. The laser-assisted eye treatment system according to claim 1, the routine further comprising planning the eye treatment in relation to data acquired on a basis of an external pretreatment characterization of the patient's eye.

\* \* \* \* \*